United States Patent
Park et al.

(10) Patent No.: US 11,628,236 B2
(45) Date of Patent: Apr. 18, 2023

(54) COMPOSITION FOR HEMOSTASIS AND CONTAINER COMPRISING SAME

(71) Applicant: DALIM TISSEN CO., LTD., Seoul (KR)

(72) Inventors: Si-Nae Park, Seoul (KR); Sang-Hee Bae, Suwon-si (KR); Jae-Hyung Ko, Seoul (KR)

(73) Assignee: DALIM TISSEN CO., LTD., Seoul (KR)

( * ) Notice: Subject to any disclaimer, the term of this patent is extended or adjusted under 35 U.S.C. 154(b) by 372 days.

(21) Appl. No.: 16/767,912

(22) PCT Filed: Nov. 28, 2018

(86) PCT No.: PCT/KR2018/014752
§ 371 (c)(1),
(2) Date: May 28, 2020

(87) PCT Pub. No.: WO2019/107887
PCT Pub. Date: Jun. 6, 2019

(65) Prior Publication Data
US 2021/0001002 A1 Jan. 7, 2021

(30) Foreign Application Priority Data

Nov. 28, 2017 (KR) .................. 10-2017-0160858
Oct. 24, 2018 (KR) .................. 10-2018-0127183

(51) Int. Cl.
*A61L 24/04* (2006.01)
*A61L 24/00* (2006.01)

(52) U.S. Cl.
CPC ......... *A61L 24/043* (2013.01); *A61L 24/0031* (2013.01); *A61L 24/0036* (2013.01); *A61L 2400/04* (2013.01)

(58) Field of Classification Search
CPC ............. A61L 24/043; A61L 24/0031; A61L 24/0036; A61L 2400/04
See application file for complete search history.

(56) References Cited

U.S. PATENT DOCUMENTS 5,464,471 A * 11/1995 Whalen ................ A61L 24/106
604/290
5,605,887 A * 2/1997 Pines .................... C07K 14/75
530/421

(Continued)

FOREIGN PATENT DOCUMENTS

JP 2002523336 A 7/2002
JP 2006 015144 A 1/2006

(Continued)

OTHER PUBLICATIONS

Office Action issued for Japanese patent application serial No. 2020-549529, dated May 11, 2021 with English machine translation.

(Continued)

*Primary Examiner* — Guy K Townsend
(74) *Attorney, Agent, or Firm* — Westman, Champlin & Koehler, P.A.; Amanda M. Prose

(57) ABSTRACT

The present invention relates to a composition for hemostasis which contains collagen, stabilizer, and thrombin, and a container including the same. The present invention is applicable to a bleeding patient requiring emergency treatment with a simple method of use. There is no toxicity and no problem of blood infection. A biodegradation rate is fast. In this regard, the present invention achieves an excellent hemostatic effect. Therefore, the composition for hemostasis is useful as a hemostat.

24 Claims, 2 Drawing Sheets

(56) References Cited

U.S. PATENT DOCUMENTS

| | | | | |
|---|---|---|---|---|
| 5,773,033 | A * | 6/1998 | Cochrum | A61K 38/39 424/530 |
| 5,883,078 | A * | 3/1999 | Seelich | C09J 189/00 530/384 |
| 8,067,031 | B2 * | 11/2011 | Daniloff | A61K 47/34 523/105 |
| 8,460,708 | B2 * | 6/2013 | Daniloff | A61K 9/1647 514/772.3 |
| 8,481,073 | B2 * | 7/2013 | Daniloff | A61L 27/50 514/772.3 |
| 8,722,039 | B2 * | 5/2014 | Preiss-Bloom | A61L 24/043 424/443 |
| 8,940,335 | B2 * | 1/2015 | Goessl | A61P 7/04 424/491 |
| 9,005,609 | B2 * | 4/2015 | Pendharkar | A61K 9/0019 424/94.64 |
| 9,084,728 | B2 * | 7/2015 | Goessl | B65B 55/02 |
| 9,327,010 | B2 * | 5/2016 | Ellis-Behnke | A61P 7/04 |
| 9,364,513 | B2 * | 6/2016 | Ellis-Behnke | A61K 38/08 |
| 9,408,945 | B2 * | 8/2016 | Goessl | A61P 7/04 |
| 9,700,650 | B2 * | 7/2017 | Gong | A61L 27/52 |
| 9,821,025 | B2 * | 11/2017 | Hedrich | A61K 38/38 |
| 9,833,541 | B2 * | 12/2017 | McCoy | A61P 17/02 |
| 10,245,348 | B2 * | 4/2019 | Goessl | A61K 38/39 |
| 10,322,170 | B2 * | 6/2019 | Gulle | A61L 26/0052 |
| 10,517,988 | B1 * | 12/2019 | Modak | A61L 24/0005 |
| 10,994,045 | B2 * | 5/2021 | Goessl | A61L 24/10 |
| 11,033,654 | B2 * | 6/2021 | Modak | A61L 26/008 |
| 2005/0123588 | A1 * | 6/2005 | Zhu | A61K 9/70 424/443 |
| 2005/0281883 | A1 * | 12/2005 | Daniloff | A61L 31/041 424/489 |
| 2007/0203062 | A1 * | 8/2007 | Ellis-Behnke | A61P 17/02 514/19.3 |
| 2009/0111734 | A1 * | 4/2009 | Ellis-Behnke | A61K 38/10 514/1.1 |
| 2012/0021058 | A1 * | 1/2012 | Goessl | A61K 9/146 424/491 |
| 2012/0121532 | A1 * | 5/2012 | Goessl | A61L 24/10 428/34.1 |
| 2012/0128653 | A1 * | 5/2012 | Goessl | A61L 24/10 424/94.64 |
| 2012/0230977 | A1 * | 9/2012 | Darmoc | A61L 17/00 530/356 |
| 2013/0045182 | A1 * | 2/2013 | Gong | A61L 26/0052 514/777 |
| 2013/0090291 | A1 * | 4/2013 | Gulle | A61L 24/043 514/13.7 |
| 2013/0096063 | A1 * | 4/2013 | Hedrich | A61K 38/42 514/13.7 |
| 2013/0096082 | A1 * | 4/2013 | Harkamp | A61M 5/19 604/82 |
| 2013/0108671 | A1 * | 5/2013 | McCoy | A61K 38/17 424/94.64 |
| 2013/0129710 | A1 * | 5/2013 | Nordhaus | A61P 7/04 536/55.1 |
| 2015/0132361 | A1 * | 5/2015 | Olson | A61L 26/0066 424/443 |
| 2015/0342581 | A1 * | 12/2015 | Mylonakis | A61L 24/0031 606/214 |
| 2016/0038627 | A1 * | 2/2016 | Olson | A61L 15/28 424/9.1 |
| 2016/0136235 | A1 * | 5/2016 | Hedrich | A61K 38/17 514/13.7 |
| 2016/0193381 | A1 * | 7/2016 | Olson | A61L 15/62 424/444 |
| 2016/0271228 | A1 * | 9/2016 | Gulle | A61K 35/32 |
| 2016/0354511 | A1 * | 12/2016 | McCoy | A61K 9/06 |
| 2018/0036338 | A1 * | 2/2018 | Sanders | A61P 43/00 |
| 2018/0361012 | A1 * | 12/2018 | Floyd | A61L 15/44 |
| 2020/0215223 | A1 * | 7/2020 | Floyd | A61L 24/08 |
| 2021/0001002 | A1 * | 1/2021 | Park | A61L 24/102 |
| 2021/0015964 | A1 * | 1/2021 | Najibi | A61L 24/0031 |
| 2021/0128778 | A1 * | 5/2021 | Barry | A61L 24/0094 |
| 2022/0017646 | A1 * | 1/2022 | Modak | A61L 26/008 |
| 2022/0143320 | A1 * | 5/2022 | Swartjes | A61L 24/043 |
| 2022/0168398 | A1 * | 6/2022 | Park | A61L 26/0066 |

FOREIGN PATENT DOCUMENTS

| | | |
|---|---|---|
| JP | 4769578 B | 6/2011 |
| JP | 2013530955 A | 8/2013 |
| JP | 2013532139 A | 8/2013 |
| JP | 2014530066 A | 11/2014 |
| JP | 2015525090 A | 9/2015 |
| JP | 2016502448 A | 1/2016 |
| JP | 2017 153975 A | 9/2017 |
| KR | 10 1213460 B1 | 12/2012 |
| KR | 10 2013 0121701 A | 11/2013 |
| KR | 10 2013 0121702 A | 11/2013 |
| WO | 98/57678 A2 | 12/1998 |
| WO | 2011/151384 A1 | 12/2011 |

OTHER PUBLICATIONS

Extended European Search Report issued for European patent application serial No. 18883961.7, dated Jul. 9, 2021.
International Search Report issued for PCT/KR2018/014752, dated May 7, 2019.
Written Opinion of the International Searching Authority issued for PCT/KR2018/014752, dated May 7, 2019.
Office Action issued for Japanese patent application serial No. 2020-549529, dated Jan. 4, 2022 with English machine translation.

* cited by examiner

[FIG. 1]
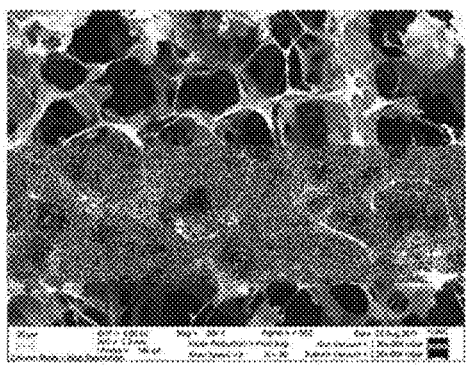
EXAMPLE 2
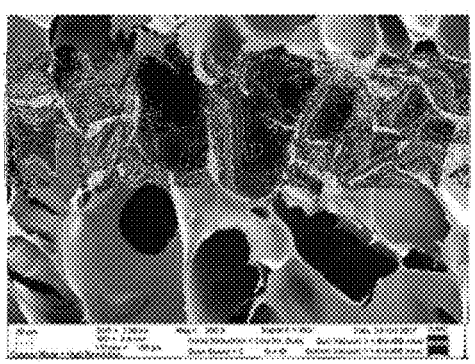
EXAMPLE 4
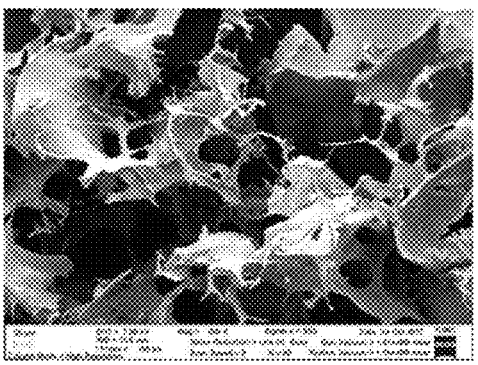
COMPARATIVE EXAMPLE 1
[FIG. 2]
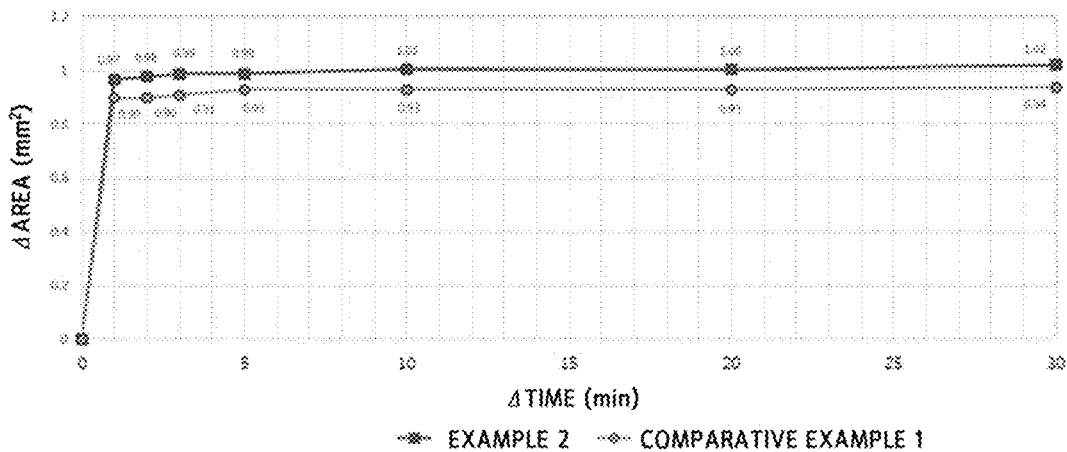

[FIG. 3]
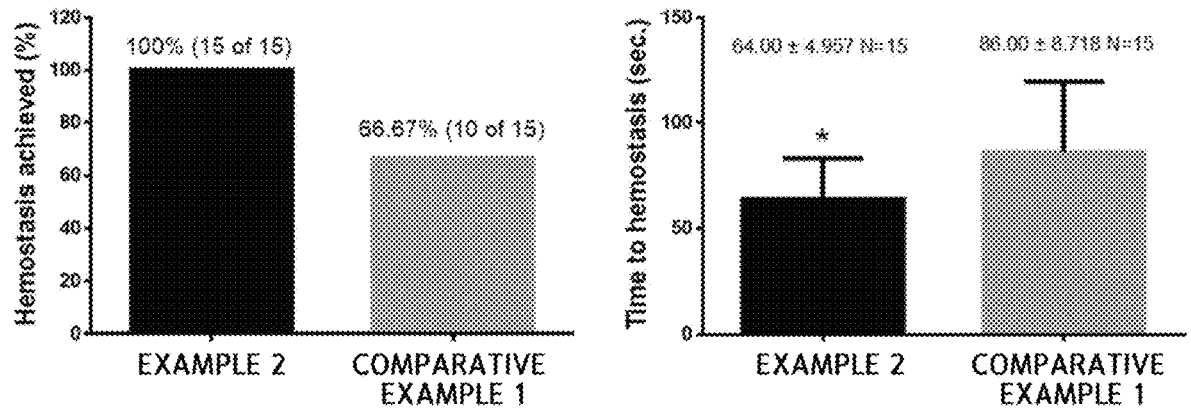
[FIG. 4]
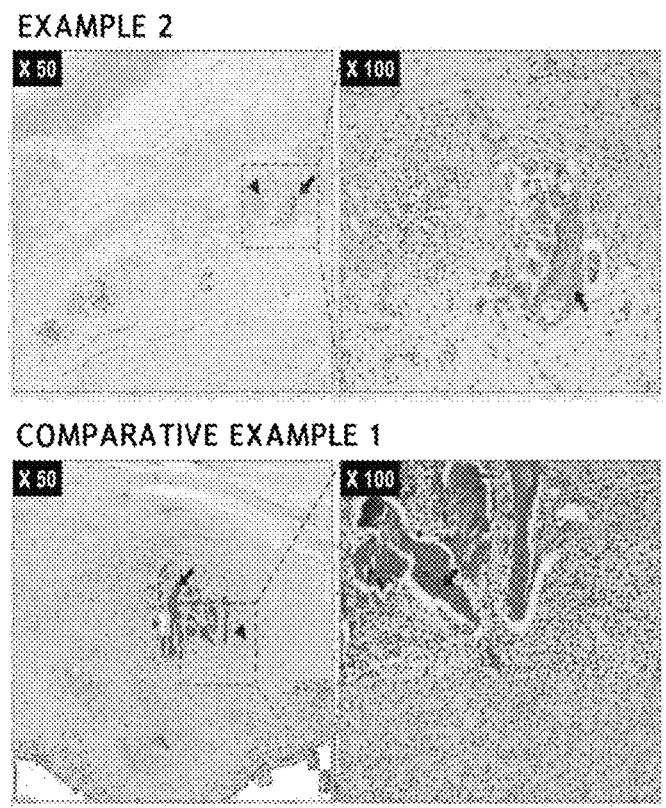

COMPOSITION FOR HEMOSTASIS AND CONTAINER COMPRISING SAME

CROSS-REFERENCE TO RELATED APPLICATION

This Application is a Section 371 National Stage Application of International Application No. PCT/KR2018/014752, filed Nov. 28, 2018, and published as WO 2019/107887 on Jun. 6, 2019, which Priority is claimed claims priority to Korean Patent Application No. 10-2017-0160858 filed on Nov. 28, 2017 and Korean Patent Application No. 10-2018-0127183 filed on Oct. 24, 2018, the entire contents of which are incorporated herein by reference.

TECHNICAL FIELD

The present invention relates to a composition for hemostasis and a container including the same.

BACKGROUND ART

A field of tissue adhesives including sealants and hemostats has been researched and developed in a rapidly growing phase. As a fibrin sealant was approved by the U.S. FDA in 1998, new tissue adhesives are constantly developed every year. The tissue adhesives are spotlighted as materials that can substitute techniques such as suturing, clipping, and cauterizing which are used in surgical or medical operations in the related art.

Although a surgical technique such as the suturing ensures strong tensile strength, the surgical technique has a problem in that a patient is caused to feel pain and a suture has to be removed after surgery. On the other hand, although the tissue adhesive has numerous advantages in that an adhesion time can be quickened, the tissue adhesive can be easily used, and the suture is not removed after the surgery, the tissue adhesive has low adhesiveness and weak tensile strength, and has limitations in that the adhesiveness is significantly degraded in a case where moisture is present. Accordingly, a method of overcoming the limitations of the tissue adhesive has been continuously researched.

Since the tissue adhesive comes into direct contact with a tissue, the tissue adhesive needs biocompatibility. In addition, in a case of a medical adhesive, the medical adhesive is usually used in a living body. Accordingly, when the adhesive intrinsically flows into body fluid and blood, the living body is directly involved. Therefore, the tissue adhesive should have no toxicity and no risk under more stringent conditions, and the tissue adhesive needs more strict biocompatibility and a biodegradable material.

The tissue adhesive which are currently commercially and/or practically available includes a cyanoacrylate instant adhesive, a fibrin glue, a gelatin glue, and polyurethanes. The cyanoacrylate instant adhesive has recently been spotlighted in the research of an instant adhesive having high functionality and high performance. In particular, a medical instant adhesive for suturing a living body tissue, which has biocompatibility, flexibility, and low toxicity has been actively researched mainly in developed countries, since the medical instant adhesive not only ensures hemostatic and antibacterial effects but also serves as an alternative of a suture.

The cyanoacrylate-based tissue adhesive is currently commercially available as a product such as Dermabond (Johnson & Johnson) and Indermil (US Surgical). The cyanoacrylate-based tissue adhesive has the following advantages. The adhesive is a single material, and is hardened by moisture without an initiator at room temperature in a short period of time. The adhesive is transparent in appearance, and has excellent adhesive strength. However, the adhesive is weak in impact, and has poor heat resistance. In addition, since toxicity of the adhesive is severe, the adhesive is rarely used at present, and is partially used in clinical practice in countries other than the United States. Furthermore, the adhesive is limitedly used due to some tissue toxicity and vulnerability.

In addition, the fibrin glue adhesive was first approved for cardiac surgery by the U.S. FDA in 1998. Thereafter, the fibrin tissue adhesive has been actively researched and developed. Currently, products such as Tisseel VH (Baxer) and Evicel™ (Johnson & Johnson) are commercially available. Together with a cyanoacrylate-based tissue adhesive, the fibrin-based tissue adhesive dominates a tissue adhesive market. In a case of the fibrin tissue adhesive, a fibrin crosslinking reaction is utilized so that fibrinogen, thrombin, calcium chloride, and an inhibitor of glandular enzyme are applied as a tissue adhesive to peripheral nerve suturing or micro blood vessel suturing. In this way, the fibrin tissue adhesive is clinically applied in order to replace or supplement the suturing. The fibrin glue adhesive has the following advantages. The fibrin glue adhesive quickly adheres to the tissue without being affected by moisture of an adhesion site. The fibrin glue adhesive does not cause a blood coagulation disorder in platelets, and has excellent biocompatibility. However, the fibrin glue adhesive the following limitations. Adhesive strength is weak, a biodegradation rate is fast, and there is a risk of blood infection.

In addition, the gelatin glue has been developed as a tissue-derived adhesive which is crosslinked with gelatin-resorcinol-formalin (GRF). In addition, the tissue adhesive such as gelatin-glutaraldehyde has been developed. However, although tissue adhesiveness is satisfactory, the tissue adhesive has the following disadvantage. The tissue adhesive results in tissue toxicity after formalin or glutaraldehyde used as a crosslinking agent causes a crosslinking reaction with proteins in a living body.

In addition, the polyurethane-based adhesive has been developed in a form of an elastic adhesive that maintains flexibility of a joint site after the adhesive is cured. The adhesive is characterized as follows. The adhesive absorbs water on a surface of living body tissues to improve adhesiveness to the tissues, and reacts with the water to be cured within several minutes. A cured product thereof has flexibility. There is an advantage in that the cured adhesive is properly biodegraded. However, there is a disadvantage in that, aromatic diisocyanate which is a synthetic raw material has biological toxicity.

In addition, although the hemostats having a collagen sole component such as 'Avitene' (Alcon) and 'Helitene' (Duhamed) are non-blood products, the materials are very expensive and have sole component. Since the materials have no tissue adhesion effect, the materials are used only as the hemostats.

As other techniques in the related art, "Fibrin monomer based tissue adhesive, U.S. Pat. No. 5,464,471, 1995", "Hemostatic and tissue adhesive, U.S. Pat. No. 5,883,078, 1999", "Fibrinogen/chitosan hemostatic agents, U.S. Pat. No. 5,773,033, 1998", and "Therapeutic fibrinogen compositions, U.S. Pat. No. 5,605,887, 1997" have been introduced. However, blood products such as fibrinogen, thrombin, blood coagulants, or aprotinin, and proteins derived from cows are used for adhesive hemostatic products. Accordingly, there is a concern about infection of specific diseases, and the techniques need excessive cost in processes for securing, storing, and manufacturing raw materials. Therefore, there is a problem in that a product price is expensive.

In addition, FloSeal (Baxter) containing a gelatin matrix component is a most frequently used product. The product shows a hemostatic effect by adding thrombin mixed in a calcium chloride solution to a gelatin matrix. The product can be used for bleeding which is not effectively controlled or cannot be controlled by ligature or through a general procedure, particularly in performing surgical operations on various regions for sites other than eyes. However, the product is largely divided into thrombin, gelatin, and calcium chloride solutions. It takes a little time, since the respective solutions are not mixed at once and have to be mixed in two steps. Therefore, in a very urgent state of serious ligation and bleeding during the surgical operation, there is no enough time for mixing the solutions in compliance with complicated product manuals. Furthermore, sequential processes may threaten a life of a bleeding patient requiring emergency treatment, and may cause a user to encounter a very cumbersome problem.

In addition, since the hemostatic products as described above are applied to humans, it is necessary to provide a highest safety standard, storage stability, and a simple direction for use for quality of a final product and components thereof. In particular, in a case where two or more components are used in combination, the hemostatic product needs to be prepared in a "ready-to-use" form, and needs to be provided in a state where the components can be easily mixed together.

As a result, it is desirable to develop the hemostat which has very little toxicity, which is easily stored and handled, which is simply used, which can be applied to bleeding patients requiring emergency treatment, and which has excellent biodegradability.

CITATION LIST

Patent Literature

[PTL 1] U.S. Pat. No. 5,464,471
[PTL 2] U.S. Pat. No. 5,773,033
[PTL 3] U.S. Pat. No. 5,605,887

DISCLOSURE

Technical Problem

In order to solve the above-described problems, the present inventors have developed a composition for hemostasis which contains collagen, stabilizer, and thrombin, and a container including the same. The present inventors have completed the present invention by confirming the followings: (i) The present invention is applicable to bleeding patients requiring emergency treatment with a simple method of use. (ii) There is no toxicity and no problem of blood infection. (iii) A biodegradation rate is fast, and (iv) the present invention achieves an excellent hemostatic effect.

Accordingly, an object of the present invention is to provide the composition for hemostasis comprising the collagen, the stabilizer, and the thrombin, and the container including the same.

In addition, another object of the present invention is to provide a hemostatic kit comprising a first container filled with the composition for hemostasis and a second container filled with diluent.

In addition, still another object of the present invention is to provide hydrogel prepared using the hemostatic kit.

Technical Solution

According to an embodiment of the present invention, in order to achieve the above-described object, there is provided a composition for hemostasis which contains collagen, stabilizer, and thrombin. In the composition for hemostasis, the stabilizer is disposed between the collagen and the thrombin so that the collagen and the thrombin are separated from each other.

The collagen may be crosslinked collagen.

The crosslinked collagen may be prepared by a method comprising (S1) a step of treating the collagen with ethanol or methanol, (S2) a step of preparing collagen solution having pH 2 to pH 4 by adding acid to the collagen treated in the step (S1), (S3) a step of preparing esterified collagen by performing centrifugation on the collagen solution prepared in the step (S2) after bringing the collagen solution into a neutral state, (S4) a step of preparing the crosslinked collagen by adding a crosslinking agent to esterified collagen prepared in the step of (S3), and (S5) a step of performing freeze-drying (lyophilization) on the crosslinked collagen prepared in the step (S4) after the crosslinked collagen is dispersed into purified water.

A molecular weight of the crosslinked collagen may be 100,000 to 1,000,000 Dalton.

The collagen may be included as much as 40 to 97 weight % in a gross weight of the composition for hemostasis.

The stabilizer may be at least one selected from a group consisting of albumin (human serum albumin), mannitol, sodium acetate ($C_2H_3NaO_2$), sucrose, trehalose, sorbitol, and glycine.

The stabilizer may be the mannitol.

The stabilizer may be included as much as 1 to 30 weight % in a gross weight of the composition for hemostasis.

The thrombin may be included as much as 2 to 50 weight % in a gross weight of the composition for hemostasis.

The composition for hemostasis may be a form of powder.

According to another embodiment of the present invention, there is provided a container including the composition for hemostasis.

According to still another embodiment of the present invention, there is provided a hemostatic kit including a first container filled with a composition for hemostasis which includes collagen, stabilizer, and thrombin, and a second container filled with diluent. In the first container, the stabilizer is disposed between the collagen and the thrombin so that the collagen and the thrombin are separated from each other.

The diluent may be at least one selected from a group consisting of purified water, calcium chloride ($CaCl_2$) solution, sodium chloride (NaCl) solution, human serum albumin, and sodium acetate ($C_2H_3NaO_2$) solution.

In this case, it is preferable that the diluent is the calcium chloride solution, and the calcium chloride may be included as much as 0.001 to 30 weight % in a gross weight of the diluent.

In the hemostatic kit, the first container and the second container may be coupled with each other so that the composition for hemostasis and the diluent are mixed with each other to form hydrogel.

An average pore size of the hydrogel may be 50 μm to 200 μm.

The hydrogel may have pH 6 to 8.

The first container may be filled with thrombin, the stabilizer, and the collagen in this order.

The composition for hemostasis in the hemostatic kit is the same as described above, and thus, description thereof will be omitted.

Advantageous Effects

The composition for hemostasis which contains the collagen, the stabilizer, and the thrombin according to the present invention achieves an excellent hemostatic effect.

In addition, the container including the composition for hemostasis which contains the collagen, the stabilizer, and the thrombin according to the present invention can be quickly and conveniently used, has no toxicity, has no problem of blood infection, has a fast biodegradation rate, and expands when coming into contact with blood. Since an expansion rate thereof is high, the hemostatic effect is excellent.

Therefore, the composition for hemostasis according to the present invention and the container including the same can be used as a hemostatic kit.

DESCRIPTION OF DRAWINGS

FIG. 1 illustrates a SEM image of each hydrogel prepared by mixing Example 2, Example 4, and Comparative Example 1 with a calcium chloride solution.

FIG. 2 illustrates a graph obtained by measuring each expansion speed for crosslinked collagen and crosslinked gelatin.

FIG. 3 illustrates a graph obtained by respectively treating Example 2 and Comparative Example 1 in a rabbit's mesenteric amputation model, and by measuring a success rate of hemostasis (left) and a time taken for the hemostasis (right).

FIG. 4 illustrates an image of a tissue obtained by H & E staining after Example 2 and Comparative Example 1 are respectively treated in a pig's superior vein cava injury model.

MODE FOR INVENTION

The present invention provides a composition for hemostasis which contains collagen, stabilizer, and thrombin. In the composition for hemostasis, the stabilizer is disposed between the collagen and the thrombin so that the collagen and the thrombin are separated from each other.

The collagen is contained in the composition for hemostasis, can absorb blood at a bleeding site, and can attract platelets to obtain a hemostatic effect. In addition, when adhering to the platelets, the collagen is not bound in a state where nothing is present, but is bound to vWF (von Willebrand's factor) which is a substance that acts as an adhesive. In this manner, the collagen promotes binding with GPIb/IX complex which is membrane glycoprotein present on a cell surface of the platelets, thereby performing primary (initial) hemostasis.

The collagen may be protein that is extracted by treating tissues of various animals with acid or alkali, or by treating enzymes such as pepsin.

The collagen may be included as much as 40 to 97 weight % in a gross weight of the composition for hemostasis. In this case, when the collagen is included less than 40 weight %, the hemostatic effect may be significantly lowered. When the collagen is included more than 97 weight %, the thrombin and the stabilizer are included relatively small. Consequently, chemical stability of the composition for hemostasis may be lowered, or the hemostatic effect may be lowered.

In addition, the collagen may be the crosslinked collagen. The crosslinked collagen preferably has a molecular weight of 100,000 to 1,000,000 Dalton, but a configuration is not limited thereto. When the molecular weight of the crosslinked collagen is less than 100,000 Dalton, blood absorption power may be fast, however, blood coagulation may be delayed so that the hemostatic effect may be lowered. When the molecular weight exceeds 1,000,000 Dalton, the blood absorption power may be significantly decreased.

The crosslinked collagen may be prepared using a chemical crosslinking method, a physical crosslinking method, or a combination thereof. In this case, the crosslinked collagen crosslinked using the chemical crosslinking method is a collagen self-crosslinked using a crosslinking agent. In contrast, the collagen crosslinked using physical crosslinking method is a collagen crosslinked using dry heat treatment, ultraviolet irradiation, and gamma ray irradiation.

Here, the crosslinking agent may be at least one of the crosslinking agents selected from a group consisting of Formaldehyde, Glutaraldehyde, Carbodiimides (EDC), and Polyepoxy compounds. The crosslinking agent is preferably the Carbodiimides (EDC), but a configuration is not limited thereto.

The crosslinked collagen has excellent mechanical strength, and may show a physical compression hemostatic effect. Accordingly, massive bleeding can be stopped.

The crosslinked collagen may be collagen obtained by crosslinking esterified collagen.

According to an embodiment of the present invention, the collagen may be prepared using a method including (S1) a step of treating the collagen with ethanol or methanol, (S2) a step of preparing collagen solution having pH 2 to pH 4 by adding acid to the collagen treated in the step (S1), (S3) a step of preparing esterified collagen by performing centrifugation on the collagen solution prepared in the step (S2) after bringing the collagen solution into a neutral state, (S4) a step of preparing the crosslinked collagen by adding a crosslinking agent to esterified collagen prepared in the step of (S3), and (S5) a step of performing freeze-drying (lyophilization) on the crosslinked collagen prepared in the step (S4) after the crosslinked collagen is dispersed into purified water.

The step (S1) is a step of treating the collagen in ethanol or methanol, and is a step of dissolving the collagen into the ethanol or the methanol so that the crosslinking agent is easily mixed therewith later. The step (S1) is a step of preparing the collagen solution.

Prior to the step (S1), the process may further include a step of extracting atelocollagen by treating animal skin tissues with an acidic solution.

The step (S2) is a step of preparing the collagen solution having pH 2 to 4 by adding the acid to the collagen treated in step (S1), and is a step of bringing the collagen into a state where the collagen completely dissolved in the ethanol or the methanol by adding the acid to the collagen solution.

The step (S3) is a step of preparing esterified collagen by performing centrifugation after the collagen solution prepared in step (S2) is brought into a neutral state. The step (S3) is a step of removing telopeptide which is a non-helical structure consisting of approximately 12 to 27 amino acids located in both ends of the collagen, and esterifying a telopeptide-removed portion. Here, the telopeptide is known to be a main cause of an immune response when the collagen is injected into a living body. Accordingly, in order to avoid the immune response when the collagen is used as a raw material for pharmaceuticals, it is preferable to use the atelocollagen or the esterified collagen by removing the telopeptide.

The step (S3) may be a step of that the pepsin enzyme is treated with the collagen solution brought into the neutral state, the telopeptide is removed, and the esterified collagen having an ester functional group is primarily prepared, and thereafter, highly purified and esterified collagen is separated by utilizing the centrifugation.

In this case, the centrifugation is preferably performed at 1,000 rpm to 30,000 rpm for 5 minutes to 3 hours so that only the esterified collagen can be deposited. However, a configuration is not limited thereto.

Here, a method of separating the highly purified and esterified collagen may include (a) a step of preparing a sample containing the telopeptide-removed atelocollagen in a container, (b) a step of causing the sample containing the atelocollagen to flow into a filtration module equipped with a filtration membrane from the container, and performing an ultrafiltration process in which pressure is applied to the filtration module so that the sample can be filtered while passing through the filtration membrane, (c) a step of collecting the esterified collagen solution flowed out of the filtration module after being filtered through the filtration membrane during the ultrafiltration process, (d) a step of determining an ultrafiltration rate by measuring a flow rate of the esterified collagen solution filtered through the filtration membrane, (e) a step of stopping the ultrafiltration process when the ultrafiltration rate decreases below a prescribed speed, (f) a step of adding water to a residue of the sample which returns to the container without passing through the filtration membrane, and thereafter, performing a diafiltration process by causing the residue to flow into the filtration module equipped with the filtration membrane, (g) a step of collecting the esterified collagen solution flowed out of the filtration module after being filtered through the filtration membrane during the diafiltration process, and (h) a step of repeatedly performing the step (f) and the step (g).

In the step (b), the sample containing the atelocollagen may be caused to flow into the filtration module equipped with the filtration membrane from the container by using a pumping action of a pump, and pressure of approximately 10 to 30 psi may be applied to the filtration module.

In the step (e), when the ultrafiltration rate is decreased to approximately 1 g/min or lower, the ultrafiltration process may be stopped.

In the step (f), the purified water as much as an amount the same as that of the solution filtered through the ultrafiltration process may be added to the residue returning to the container.

It is desirable that the diafiltration process in steps (f) and (g) is performed at least five times.

Accordingly, while esterifying the atelocollagen through steps (a) to (h), the highly purified and esterified collagen may be obtained.

Meanwhile, the step (S4) is a step of preparing the collagen crosslinked by adding the crosslinking agent to the esterified collagen prepared in step (S3), and is a step of providing the crosslinked collagen which does not cause the immune response, and shows physical compression hemostatic effect by crosslinking of the esterified collagen.

In addition, as described above, the crosslinking agent in step (S4) may be at least one of the crosslinking agents selected from a group consisting of Formaldehyde, Glutaraldehyde, Carbodiimides (EDC), and Polyepoxy compounds, and detailed description thereof will be omitted.

The step (S5) is a step of performing freeze-drying (lyophilization) after dispersing the crosslinked collagen prepared in step (S4) into the purified water, and is a step of removing the crosslinking agent remaining in the crosslinked collagen and the collagen from which the telopeptide is not removed. Therefore, in step (S5), the crosslinked collagen prepared in step (S4) is dispersed into the purified water. In this manner, a small amount of the crosslinking agent and the collagen from which the telopeptide is not removed are dissolved in the purified water. The crosslinking agent and the collagen may be frozen and removed while being in dissolved in purified water through the freeze-drying. In addition, the freeze drying may be a general method used in the related art.

The stabilizer is contained in the composition for hemostasis, and the stabilizer is disposed between the collagen and the so that the collagen and the thrombin are not mixed with each other, thereby maintaining unique properties of the proteins. Therefore, since the stabilizer is contained in the composition for hemostasis, the collagen and the thrombin which show a strong a hemostatic effect are separated from each other. Moreover, maintaining chemical stability and biological activity of the composition for hemostasis may be guaranteed with an inactive substance.

The stabilizer may be at least one selected from a group consisting of albumin (human serum albumin), mannitol, sodium acetate ($C_2H_3NaO_2$), sucrose, trehalose, sorbitol, and glycine.

In this case, the stabilizer may contain at least one selected from the group consisting of albumin, mannitol, and sodium acetate. Accordingly, chemical stability and biological activity of the thrombin may be maintained.

In addition, the stabilizer may contain at least one selected from the group consisting of mannitol, sucrose, trehalose, sorbitol, and glycine. Accordingly, a hemostasis time may be prevented from being lengthened, and blood coagulation activity may be maintained.

The stabilizer is preferably mannitol, but a configuration is not limited thereto.

The mannitol is a white needle-shaped or columnar crystal widely present in plants such as roots of mushrooms and pomegranates. The mannitol is soluble in water, is used as a laxative, and is used as a substitute for glycerol.

The stabilizer may be included as much as 1 to 30 weight % in the gross weight of the composition for hemostasis. In this case, in a case where the stabilizer is included less than 1 weight %, the collagen and the thrombin are less likely to be separated from each other, and the chemical stability may be degraded. In a case where the stabilizer is included more than 30 weight %, the collagen and the thrombin are included relatively less. Consequently, the hemostatic effect of the composition for hemostasis may be lowered.

The thrombin is included in the composition for hemostasis, and participates in blood coagulation as a powerful hemostatic factor. The thrombin hydrolyzes soluble fibrinogen in the blood, accordingly, acts as a catalyst in the reaction to convert the soluble fibrinogen into insoluble fibrin. In addition, the thrombin may induce platelet activation in a process in which fibrin is formed by activation of a blood clotting factor, which is a secondary hemostatic process.

The thrombin may be included as much as 2 to 50 weight % in the gross weight of the composition for hemostasis. In this case, in a case where the thrombin is included less than 3 weight %, the hemostatic effect may be significantly lowered. In a case where the thrombin is included more than 50 weight %, the collagen and the stabilizer may be included relatively less. Consequently, the chemical stability of the composition for hemostasis may be lowered, or the hemostatic effect may be lowered.

The composition for hemostasis may be in a form of powder. It is preferable that the composition for hemostasis in a form of dried powder is prepared in a manner that the powder is not easily deteriorated to a liquid state due to an external environment and moisture. The composition for hemostasis is in the form of powder, and the chemical stability thereof may be ensured by the respective components. It may be preferable that the powder is maintained in a state where the components are not mixed with each other. In addition, the powder has an advantage of convenient handling and storage.

According to another embodiment of the present invention, a container including the composition for hemostasis may be provided.

In this case, the container including the composition for hemostasis is filled with all of the collagen, the stabilizer, and the thrombin which show the hemostatic effect. Accordingly, a method of use is very simple, and there is an advantage in that the container is applicable to a bleeding patient requiring emergency treatment. In particular, in an urgent condition where severe ligation and bleeding occur during a surgical operation, the container may be mixed with the diluent, and may be directly applied to a bleeding site. Accordingly, the container is convenient to users, and even a non-professional technician can easily use the container. There is an advantage in that the method of use is very simple.

According to another embodiment of the present invention, there is provided a hemostatic kit including a first container filled with the composition for hemostasis which contains the collagen, the stabilizer, and the thrombin, and a second container filled with diluent. In the first container of the hemostatic kit, the stabilizer is disposed between the collagen and the thrombin so that the collagen and the thrombin are separated from each other.

The hemostatic kit uses the composition for hemostasis described above. Accordingly, the collagen, the stabilizer, and the thrombin are the same as described above. Therefore, hereinafter, detailed description thereof will be omitted.

The first container is filled with the composition for hemostasis, and the stabilizer is disposed between the collagen and the thrombin. Accordingly, it is not desirable that a disposition order is changed by an external physical force. In addition, depending on the order for disposing the collagen, the stabilizer, and the thrombin which fill the first container, flowability of the mixture with the diluent may vary. Moreover, an expansion rate and an expansion speed may vary. Accordingly, it is preferable that the first container is filled with the collagen—the stabilizer—the thrombin, or the thrombin—the stabilizer—the collagen in this order. More preferably, the first container is filled with the thrombin, the stabilizer, and the collagen in this order. However, a configuration is not limited thereto.

The second container is filled with the diluent. In this case, the diluent may be used as a solvent or a dispersion medium for dissolving or dispersing the composition for hemostasis of the first container. For example, the diluent may be at least one selected from a group consisting of purified water, calcium chloride ($CaCl_2$) solution, sodium chloride (NaCl) solution, human serum albumin, and sodium acetate ($C_2H_3NaO_2$) solution. Preferably, the diluent may be the calcium chloride solution or the sodium chloride solution. However, a configuration is not limited thereto.

In a case where the diluent is the calcium chloride solution, the calcium chloride may be included as much as 0.001 to 30 weight % in the gross weight of the diluent. As long as the diluent is well mixed with the composition for hemostasis in any range of weight %, the range is not particularly limited.

A shape and a material of the first container or the second container are not particularly limited, and may adopt those commonly used in pharmaceutical and biotechnology fields. For example, the shape of the first container or the second container may be a syringe, and the material of the first container or the second container may be a material that does not cause a chemical reaction with any one selected from the collagen, the stabilizer, and the thrombin.

Meanwhile, in the hemostatic kit, the first container and the second container may be coupled with each other, and thus the composition for hemostasis and the diluent may be mixed with each other to form the hydrogel.

The first container may include a fastening protrusion in a front end of the first container so that the first container and the second container can be coupled with each other. The second container may include a fastening groove to be coupled with the fastening protrusion in the front end of the first container.

In addition, the hydrogel may be porous. Accordingly, when used as a hemostat, a blood absorption rate is high, and a form of the hydrogel is maintained even after the blood is absorbed. Therefore, the hemostatic effect is not degraded, and an excellent hemostatic effect may be achieved.

In addition, an average pore size of the hydrogel may be 50 μm to 200 μm. When the average pore size is smaller than 50 μm, the blood absorption rate may decrease. When the average pore size exceeds 200 μm, the hemostatic effect may be degraded, since the form of the hydrogel cannot be maintained after the blood is absorbed.

In addition, a time for forming the hydrogel may be 5 seconds to 5 minutes so that the time can prevent serious ligation and bleeding in a very urgent condition. In addition, since the hydrogel is formed in a short time, a user can easily use the hemostatic kit.

The hydrogel has pH in a neutral state when the composition for hemostasis and the diluent are mixed with each other. Accordingly, biocompatibility and biosafety may be ensured when the hydrogel is applied to a living body. In addition, the hydrogel has low toxicity, and may ensure safety from infection. Accordingly, the hydrogel may have pH of 6 to 8.

Hereinafter, preferred embodiments will be presented to facilitate understanding of the present invention. However, the following embodiments are only illustrative of the present invention. It is apparent to those skilled in the art that the present invention can be modified and corrected in various ways within the scope and the technical idea of the present invention. As a matter of course, the modifications and the corrections are included in the appended claims.

Preparing Example 1: Preparing Esterified Collagen Powder

Esterified collagen powder was manufactured through the following processes.

(1) The collagen was added to ethanol, and was stirred in a refrigerated state.

(2) The pH of the sample was adjusted to 6.7±0.3 by using 0.5M HCl.

(3) The solution was placed in dialysis tubing, and dialysis was performed by using the purified water.

(4) The solution was subjected to freezing and freeze-drying to obtain the esterified collagen powder.

Preparing Example 2: Preparing Crosslinked Collagen

The crosslinked collagen powder was prepared through the following processes.

(1) The esterified collagen prepared in Preparing Example 1 was placed in the purified water, and is stirred therein.

(2) EDC (1-ethyl-3-(3-dimethylaminopropyl)-carbodiimide) was placed in the sufficiently mixed esterified collagen solution.

(3) EDC was mixed well enough to react with the esterified collagen.

(4) The mixture was left unattended in a refrigerated state for 2-3 days.

(5) The crosslinked and cured collagen solution was placed in the purified water, and was dispersed therein.

(6) When the crosslinked collagen solution is left unattended and layer separation occurs, only the crosslinked collagen is collected, and the solution is discarded.

(7) The process (6) above was repeated 3 to 5 times to obtain only the crosslinked collagen.

(8) The cross-linked collagen was placed in buffer (sodium phosphate/sodium chloride), and was left unattended in the refrigerator for 1-2 days so that the buffer is neutralized.

(9) After the buffer was neutralized, the buffer was cleaned with the purified water, and the collagen was subjected to freezing and freeze-drying.

(10) The sample subjected to freeze drying was placed in and ground by a blender.

(11) The powder was filtered through a sieve to select particles having a size of 200 to 355 μm.

Preparing Example 3: Crosslinked Gelatin

The crosslinked gelatin was obtained using commercially available gelatin powder (FloSeal Hemostatic Matrix, Baxter A.G., USA) instead of the esterified collagen powder.

Experimental Example 1: Confirming Flowability

In order to confirm a difference in flowability when mixed with the calcium chloride solution (concentration) serving as the diluent in accordance with the disposition order of the collagen, mannitol, and thrombin in the composition for hemostasis, examples were prepared as illustrated in Table 1 below. In this case, the mannitol and the thrombin were commercially available products in a form of powder. One obtained in Preparing Example 1 was used as the esterified collagen, and one obtained in Preparing Example 2 was used as the crosslinked collagen. In addition, the crosslinked gelatin obtained in Preparing Example 3 was used to perform a comparative analysis on the flowability as Comparative Example 1.

TABLE 1

| Classification | Disposition Order |
| --- | --- |
| Example 1 | crosslinked collagen - mannitol - thrombin |
| Example 2 | thrombin - mannitol - crosslinked collagen |
| Example 3 | esterified collagen - mannitol - thrombin |
| Example 4 | thrombin - mannitol - esterified collagen |
| Comparative Example 1 | thrombin - mannitol - crosslinked gelatin |

Examples 1 to 4 and Comparative Example 1 were prepared as illustrated in Table 1 above. Results obtained by measuring forces required for mixing through the following method were illustrated in Table 2.

(1) Two syringes were prepared, and one syringe was filled in Examples 1 to 4 or Comparative Example 1 in the disposition order illustrated in Table 1, and the other syringe was filled with the calcium chloride solution.

(2) The syringes were connected to each other (ends of the syringes were screwed to and coupled with each other).

(3) The syringe filled with Examples 1 to 4 or Comparative Example 1 was fixed (pinched) using a machine.

(4) Using a machine, a plunger of the syringe (female type) filled with the calcium chloride solution was pushed using a machine, and was screwed to the syringe filled with Examples 1 to 4 or Comparative Example 1.

(5) An empty syringe was fixed to (pinched by) a machine by changing a position of the syringe.

(6) The plunger of the syringe (male type) filled with the mixed contents was pushed to insert the mixed contents into the empty syringe.

(7) The steps (4) to (5) were repeated to measure the forces required for mixing. Here, the required forces (N1, N3, N5, and N7) were measured each time the step (4) is performed.

Meanwhile, the composition for hemostasis which fills the syringe was solid powder. Accordingly, the syringe was filled to have high density. Therefore, the force required for injecting the calcium chloride solution into the syringe filled with the composition for hemostasis is relatively stronger than the force required for injecting the composition for hemostasis into the syringe filled with the calcium chloride solution. Accordingly, the required forces (N1, N3, N5, and N7) for injecting the calcium chloride solution into the syringe filled with the composition for hemostasis were measured to confirm a difference in the flowability during the mixing.

TABLE 2

| Number of Mixing Times | Maximum Value of Force Loaded (N) | | | | |
| --- | --- | --- | --- | --- | --- |
| | Example 1 | Example 2 | Example 3 | Example 4 | Comparative Example 1 |
| N1 | 4.36 | 3.94 | 22.57 | 21.84 | 19.43 |
| N3 | 10.83 | 7.05 | 5.12 | 13.1 | 8.39 |
| N5 | 10.18 | 6.52 | 5.83 | 21.98 | 61.07 |
| N7 | 9.97 | 7.04 | 22.32 | 7.69 | 22.16 |
| Average | 8.84 | 6.14 | 13.96 | 16.15 | 27.76 |

As illustrated in Table 2, the forces required for the mixing, that is, magnitudes of the pressure generated during the mixing Examples 1 to 4 were relatively smaller than that of Comparative Example 1. Meanwhile, on average, the magnitude of the pressure generated during the mixing in Example 2 was smaller than that of Example 1. Accordingly, it was confirmed as follows. When the thrombin and the mannitol were disposed on an inlet side of the syringe, the pressure required for mixing the raw materials was reduced from an initial stage of the mixing, thereby assisting the raw materials to be mixed well.

In contrast, Comparative Example 1 filled with crosslinked gelatin did not show a constant or significant pattern, unlike Examples 1 to 4. In a case of the crosslinked gelatin, on average and entirely, the magnitude of the pressure generated during the mixing was greater than those in Example 1 which was filled with the crosslinked collagen, and Example 2 to Example 4. In N5, the significant differences were shown as much as approximately 3 times to approximately 10 times.

Experimental Example 2: Confirming Microstructure Through Scanning Electron Microscope (SEM)

After Experimental Example 1 was performed, Example 2, Example 4, and Comparative Example 1 in which the calcium chloride solution is mixed were performed using SEM so as to obtain each microstructure image. The image is illustrated in FIG. 1.

As illustrated in FIG. 1, Example 2 and Example 4 showed a fine and dense porous membrane structure. On the other hand, Comparative Example 1 showed less porous membrane structure than Example 2 and Example 4, and the structure was tangled without order. Accordingly, it was confirmed as follows. Compared to Comparative Example 1, Example 2 and Example 4 relatively have more uniform porous membrane structure when mixed with the calcium chloride solution. Therefore, the blood is absorbed and coagulates well to assist the hemostasis.

Experimental Example 3: Confirming Expansion Rate and Expansion Speed

In order to confirm the expansion speed indicated after the composition for hemostasis according to the present invention is mixed with the diluent, Example 2 and Comparative Example 1 were first respectively prepared in accordance with the method illustrated in Table 1 of Experimental Example 1. Particle areas of the prepared Example 2 and Comparative Example 1 were respectively measured. Thereafter, after each sample was mixed with the calcium chloride solution, the particle areas were measured at intervals of 1, 2, 3, 5, 10, 20, and 30 minutes. Area change rates were calculated to calculate the expansion speed. The results are illustrated in FIG. 2.

As illustrated in FIG. 2, in Example 2 and Comparative Example 1, the samples were rapidly expanded within 1 minute, and were continuously expanded up to 2, 3, 5, and 10 minutes. However, it was confirmed that the expansion rate was saturated after 10 minutes. In addition, Example 2 including the crosslinked collagen showed a faster expansion rate and a larger area change than those of Comparative Example 1. Accordingly, the crosslinked collagen causes the particles to be expanded faster within the same time than the crosslinked gelatin. In this manner, it is confirmed that the physical compression action may be very helpful for the hemostatic effect.

Experimental Example 4: Degradability Test

The biodegradability and the degradability of the collagen contained in the composition for hemostasis according to the present invention were measured. A degradability test was performed to confirm whether the collagen has the biocompatibility or whether the collagen has low degradability and no risk of infection. First, the esterified collagen obtained from Preparing Example 1, the crosslinked collagen obtained from Preparing Example 2, and the crosslinked gelatin obtained from Preparing Example 3 were prepared to measure the weight of each sample. Thereafter, each sample was placed in a micro-centrifuge tube, and the micro-centrifuge tube is filled with 1 to 2 mL of 1×PBS buffer containing 25 units/mL of the collagen degrading enzyme (Collagenase). The tube containing the sample was placed in a water bath of 37° C., and was left unattended for 24 to 72 hours. After 24, 48, and 72 hours, the sample was taken out, and the weight of the sample was measured after freeze-drying. A remaining weight ratio of the sample measured before and after the degradation test was calculated using the following formula. The results are illustrated in Table 3.

<Formula of Remaining Weight Ratio>

Remaining weight ratio (%)=dry weight of sample after degradation test/dry weight of sample before degradation test*100

TABLE 3

| Classification | Weight Ratio (%) Remaining after Each Biodegradation Time | | |
|---|---|---|---|
| | 24 hours later | 48 hours later | 72 hours later |
| Crosslinked collagen | 73.0 ± 3.1 | 38.7 ± 1.2 | 0 |
| Esterified collagen | 68.0 ± 2.0 | 34.6 ± 1.2 | 0 |
| Crosslinked gelatin | 79.0 ± 2.3 | 43.3 ± 3.0 | 3.3 ± 1.2 |

It was confirmed that in the crosslinked collagen and the esterified collagen, the sample was completely degraded within 72 hours by the collagen degrading enzyme. On the other hand, in the crosslinked gelatin, the remaining weight ratio is 3.3±1.2% after 72 hours, and the sample was not completely degraded by the collagen degrading enzyme. Accordingly, it was confirmed that the crosslinked collagen and the esterified collagen have faster degradation capability under the same condition than the crosslinked gelatin. Therefore, it was confirmed that the biodegradability of the crosslinked collagen and the esterified collagen is high and the risk of infection thereof is very low.

Experimental Example 5: Comparison of Hemostatic Ability in Rabbit's Mesenteric Amputation Model In order to confirm the hemostatic ability of the composition for hemostasis according to the present invention, Example 2 and Comparative Example 1 were prepared in the same manner as in Experimental Example 1. The hemostatic ability was compared using the rabbit's mesenteric amputation model. After the mesentery was amputated to induce bleeding, Example 2 or Comparative Example 1 was applied thereto. Thereafter, hemostatic compression was attempted for 30 seconds to confirm whether there is bleeding. In a case where there is the bleeding, the hemostatic compression was additionally repeated for 30 seconds. The probability that the hemostasis may be successful within 90 seconds and the time required for the hemostasis were measured. The results are illustrated in FIG. 3.

As illustrated in FIG. 3, Example 2 showed successful hemostasis in all 15 rabbits within 90 seconds. On the other hand, Comparative Example 1 showed completed hemostasis in only 10 of the 15 rabbits within 90 seconds. In addition, the hemostasis time was 64±4.957 seconds in Example 2. On the other hand, the hemostasis time was measured as 86±8.718 seconds in Comparative Example 1. Statistical significance was confirmed by the t-test (p<0.05). Accordingly, in a case where the composition for hemostasis according to the present invention was used, a hemostasis success rate was high, and the hemostasis time was shortened. Therefore, it was confirmed that the present invention achieves excellent hemostatic ability.

Experimental Example 6: Comparison of Biodegradability and Inflammatory Response in Pig's Superior Vein Cava Injury Model Example 2 and Comparative Example 1 were prepared in the same manner as in Experimental Example 1 in order to confirm the biodegradation and the inflammatory response of the composition for hemostasis according to the present invention. Bleeding was induced by partially incising a pig's superior vein cava. Example 2 or Comparative Example 1 was applied to perform the hemostasis. After one week from the experiment, a sample was collected by sacrificing the pig. The remaining amount of the hemostatic composition and the inflammatory response were compared through H & E staining. The results are illustrated in Table 4 below, and tissue images after the H & E staining are illustrated in FIG. 4.

TABLE 4

|  | Example 2 | Comparative Example 1 |
|---|---|---|
| Inflammatory reaction | + | ++ |
| Residue | + | ++ |

(In Table 4 above, + means mild, and ++ means moderate.) As illustrated in Table 4, the residue of the composition for hemostasis used in the pig's superior vein cava injury model was left mild in Example 2, and was left moderate in Comparative Example 1. In proportion to the amount of the residue, Example 2 showed a mild inflammatory response, and Comparative Example 1 showed a moderate inflammatory response.

In addition, FIG. 4 illustrates the respective tissue images after H & E staining in Example 2 and Comparative Example 1. It was confirmed that the amount of the residue in Example 2 was relatively smaller than the amount of the residue in Comparative Example 1. It can be understood that the number of inflammatory cells in Example 2 was smaller than those in Comparative Example 1 in proportion to the amount of the residue. As shown in the result of Experimental Example 4, a composition having fast degradation capability has high biodegradability and a low risk of infection such as the inflammatory response. Accordingly, in a case where the composition for hemostasis according to the present invention is used, the biocompatibility is improved, and side effects are reduced. Therefore, it is possible to minimize the risk that the hemostat may newly cause infection.

Experimental Example 7: Confirming Biocompatibility of Composition for Hemostasis in White Rat's Heminephrectomy Model Example 2 and Comparative Example 1 were prepared in the same manner as in Experimental Example 1 in order to confirm the biocompatibility of the composition for hemostasis according to the present invention. Bleeding was induced by partially incising a white rat's kidney. Thereafter, Example 2 or Comparative Example 1 was applied to perform the hemostasis. After one week from the experiment, a sample was collected by sacrificing the white rat. The biocompatibility depending on a difference of the composition for hemostasis was compared and confirmed through pathological spectrometry. The results are illustrated in Table 5 below.

TABLE 5

| | | Levels | | | |
|---|---|---|---|---|---|
| | | Example 2 | | Comparative Example 1 | |
| Tissue | Evaluation Index | Sample 1 | Sample 2 | Sample 1 | Sample 2 |
| Renal cortex | Tissue alteration, bleeding | 0 | 0 | 2 | 1 |
| | Epithelial regressive changes (edema, necrosis) | 0 | 0 | 3 | 1 |
| | Glomerular necrosis | 0 | 0 | 0 | 0 |
| | Glomerular hyaline microthrombi | 0 | 0 | 0 | 0 |
| | Inflammation | 4 | 4 | 5 | 5 |
| | Extraglomerular hemorrhage | 0 | 0 | 0 | 0 |
| | Intraglomerular hemorrhage | 0 | 0 | 0 | 0 |
| | Fibroblast activation | 2 | 2 | 3 | 3 |
| | Fibrosis | 2 | 1 | 3 | 3 |
| | Fistula | 0 | 0 | 0 | 0 |
| | Microvascular proliferation | 2 | 2 | 2 | 1 |
| | Hyaline in the tubules | 2 | 1 | 2 | 1 |
| | Interstitial hemorrhage | 1 | 0 | 2 | 3 |
| | Polymorphonuclears | 3 | 3 | 2 | 2 |
| | Collagen scar | 0 | 0 | 0 | 0 |
| Extra fat tissue | Granuloma/inflammation around kidney | 2 | 4 | 4 | 5 |
| | Destruction score | 18 | 17 | 28 | 25 |

Levels in Table 5 above were assigned in accordance with the following criteria: 0: no change
   1: minimal (very slight change)
   2: mild (light or little change)
   3: moderate (modest change)
   4: marked (distinct change)
   5: maximum (supreme or extreme change)

As illustrated in Table 5, postoperative tissue deformation and postoperative bleeding were observed in a case of the white rat to which Comparative Example 1 was applied. However, the postoperative tissue deformation or the postoperative bleeding was not observed in a case of the white rat to which Example 2 was applied. Fibroblast activity or fibrosis caused by fibroblast proliferation more greatly occurred in the sample to which Comparative Example 1 was applied, and intercellular bleeding greatly occurred in Comparative Example 1. In particular, the granuloma and the inflammatory response were significantly observed in the adipose tissue around the nephrectomy surface to which Comparative Example 1 was applied.

On the other hand, a destruction score serving as an index indicating a pathological risk showed an average of 17.5 in Example 2 and an average of 26.5 in Comparative Example 1. As a result, it can be understood that the biocompatibility of Example 2 is more excellent than that of Comparative Example 1.

The invention claimed is:

1. A composition for hemostasis comprising collagen; stabilizer; and
thrombin, wherein the composition is provided with layered components in a container where the stabilizer is provided in a layer between a layer of the collagen and a layer of the thrombin,
wherein the collagen, the stabilizer and the thrombin are a form of dried powder respectively, and
wherein the composition for hemostasis is a form of dried powder.

2. The composition of claim 1, wherein the collagen is crosslinked collagen.

3. The composition of claim 2, wherein the crosslinked collagen is prepared using a preparing method including
(S1) a step of treating the collagen with ethanol or methanol,
(S2) a step of preparing collagen solution having pH 2 to pH 4 by adding acid to the collagen treated in the step (S1),
(S3) a step of preparing esterified collagen by performing centrifugation on the collagen solution prepared in the step (S2) after bringing the collagen solution into a neutral state,
(S4) a step of preparing the crosslinked collagen by adding a crosslinking agent to esterified collagen prepared in the step of (S3), and
(S5) a step of performing freeze drying on the crosslinked collagen prepared in the step (S4) after the crosslinked collagen is dispersed into purified water.

4. The composition of claim 2, wherein a molecular weight of the crosslinked collagen is 100,000 to 1,000,000 Dalton.

5. The composition of claim 1, wherein the collagen is included as much as 40 to 97 weight % in a gross weight of the composition for hemostasis.

6. The composition of claim 1, wherein the stabilizer is at least one selected from a group consisting of albumin (human serum albumin), mannitol, sodium acetate ($C_2H_3NaO_2$), sucrose, trehalose, sorbitol, and glycine.

7. The composition of claim 1, wherein the stabilizer is the mannitol.

8. The composition of claim 1, wherein the stabilizer is included as much as 1 to 30 weight % in a gross weight of the composition for hemostasis.

9. The composition of claim 1, wherein the thrombin is included as much as 2 to 50 weight % in a gross weight of the composition for hemostasis.

10. A container comprising:
the composition for hemostasis according to claim 1.

11. A hemostatic kit comprising:
a first container filled with a composition for hemostasis comprising collagen, stabilizer, and thrombin; and
a second container filled with diluent,
wherein in the first container, the composition is provided with layered components in a container where the stabilizer is provided in a layer between a layer of the collagen and a layer of the thrombin,
wherein the collagen, the stabilizer and the thrombin are a form of dried powder respectively, and
wherien the composition for hemostatis is a form of dried powder.

12. The kit of claim 11, wherein the diluent is at least one selected from a group consisting of purified water, calcium chloride ($CaCl_2$) solution, sodium chloride (NaCl) solution, human serum albumin, and sodium acetate ($C_2H_3NaO_2$) solution.

13. The kit of claim 12, wherein the diluent is the calcium chloride solution, and the calcium chloride is included as much as 0.001 to 30 weight % in a gross weight of the diluent.

14. The kit of claim 11, wherein in the hemostatic kit, the first container and the second container are coupled with each other so that the composition for hemostasis and the diluent are mixed with each other to form hydrogel, and an average pore size of the hydrogel is 50 μm to 200 μm.

15. The kit of claim 14, wherein the hydrogel has pH 6 to 8.

16. The kit of claim 11, wherein the first container is filled with thrombin, the stabilizer, and the collagen in this order.

17. The kit of claim 11, wherein the collagen is crosslinked collagen.

18. The kit of claim 17, wherein the crosslinked collagen is prepared using a preparing method including
(S1) a step of treating the collagen with ethanol or methanol,
(S2) a step of preparing collagen solution having pH 2 to pH 4 by adding acid to the collagen treated in the step (S1),
(S3) a step of preparing esterified collagen by performing centrifugation on the collagen solution prepared in the step (S2) after bringing the collagen solution into a neutral state,
(S4) a step of preparing the crosslinked collagen by adding a crosslinking agent to esterified collagen prepared in the step of (S3), and
(S5) a step of performing freeze drying on the crosslinked collagen prepared in the step (S4) after the crosslinked collagen is dispersed into purified water.

19. The kit of claim 17, wherein a molecular weight of the crosslinked collagen is 100,000 to 1,000,000 Dalton.

20. The kit of claim 11, wherein the collagen is included as much as 40 to 97 weight % in a gross weight of the composition for hemostasis.

21. The kit of claim 11, wherein the stabilizer is at least one selected from a group consisting of albumin (human serum albumin), mannitol, sodium acetate ($C_2H_3NaO_2$), sucrose, trehalose, sorbitol, and glycine.

22. The kit of claim 21, wherein the stabilizer is the mannitol.

23. The kit of claim 11, wherein the stabilizer is included as much as 1 to 30 weight % in a gross weight of the composition for hemostasis.

24. The kit of claim 11, wherein the thrombin is included as much as 2 to 50 weight % in a gross weight of the composition for hemostasis.

* * * * *